United States Patent [19]

Pelosi, Jr.

[11] 4,066,669
[45] Jan. 3, 1978

[54] DIETHYL ACETAMIDO[5-(4-NITROPHENYL)FURFURYL]MALONATE

[75] Inventor: Stanford S. Pelosi, Jr., Norwich, N.Y.

[73] Assignee: Morton-Norwich Products, Inc., Norwich, N.Y.

[21] Appl. No.: 776,649

[22] Filed: Mar. 11, 1977

[51] Int. Cl.$^2$ .......................................... C07D 307/54
[52] U.S. Cl. ............................ 260/347.5; 260/347.4; 424/285
[58] Field of Search ........................... 260/347.4, 347.5

[56] References Cited

U.S. PATENT DOCUMENTS 3,282,965  11/1966  Szarvasi et al. ............... 260/347.7 X

*Primary Examiner*—Richard L. Raymond
*Attorney, Agent, or Firm*—Anthony J. Franze

[57] ABSTRACT

Diethyl acetamido[5-(4-nitrophenyl)furfuryl]malonate is useful as an anthelmintic agent.

1 Claim, No Drawings

DIETHYL ACETAMIDO[5-(4-NITROPHENYL)FURFURYL]MALONATE

This invention relates to the compound diethyl acetamido[5-(4-nitrophenyl)furfuryl]malonate of the formula:

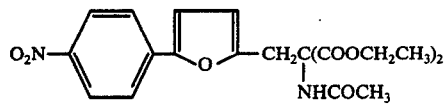

and a method for its preparation.

The compound of this invention is distinguished by its ability to combat helminth infection. When administered by gavage as a suspension in aqueous solution to mice harboring *Syphacia obvelata* worms, this compound accomplished a 70% reduction of the worm burden at a dose of 300 mg/kg. The compound of this invention can be combined in obvious forms such as suspensions and dispersions to provide conveniently administered dosage compositions.

The compound of this invention is readily prepared. Currently, it is preferred to react diethyl acetamidomalonate and 5-(4-nitrophenyl)furfuryl chloride in the presence of sodium and a solvent such as ethanol.

In order that this invention may be fully available to and understood by those skilled in the art, the method now preferred for making it is described:

To 300 ml of absolute ethanol was added in portions 2.4 g (0.104 mole) of sodium followed by 21.7 g (0.10 mole) of diethyl acetamidomalonate and stirring was continued for 10 minutes. 5-(4-Nitrophenyl)furfuryl chloride (23.7 g, 0.10 mole) was then added in portions, and the mixture was heated under reflux for 5 hrs. The mixture was filtered hot to remove the insoluble sodium chloride. The filtrate was cooled in a refrigerator, and the solid which was deposited was collected by filtration and washed with ether. The solid was stirred in water, collected by filtration, and dried in an oven at 100° for 2 hrs. to give 21 g (50%) of diethyl acetamido[5-(4-nitrophenyl)furfuryl]malonate. Recrystallization from SDA-32 gave an analytical sample, m.p. 183°–185°.

Anal. Calcd. for $C_{20}H_{22}N_2O_8$: C, 57.41; H, 5.30; N, 6.70. Found: C, 57.38; H, 5.27; N, 6.63.

What is claimed is:

1. The compound diethyl acetamido[5-(4-nitrophenyl)furfuryl]malonate.